United States Patent [19]

Kranys

[11] Patent Number: 5,405,338
[45] Date of Patent: Apr. 11, 1995

[54] HELICALLY WOUND CATHETERS

[75] Inventor: Rudy J. Kranys, Coconut Grove, Fla.

[73] Assignee: Cordis Corporation, Miami Lakes, Fla.

[21] Appl. No.: 109,081

[22] Filed: Aug. 19, 1993

[51] Int. Cl.⁶ ............................................. A61M 25/00
[52] U.S. Cl. ....................................... 604/282; 604/96; 604/53
[58] Field of Search ...................... 604/93, 96, 97, 98, 604/101, 103, 104, 264, 280, 282; 606/194

[56] References Cited

U.S. PATENT DOCUMENTS

| | | | |
|---|---|---|---|
| 1,477,695 | 12/1923 | Dolge et al. | 604/264 |
| 2,211,975 | 8/1940 | Hendrickson . | |
| 2,330,399 | 9/1943 | Winder . | |
| 3,428,046 | 2/1969 | Remer et al. | 604/96 |
| 3,485,234 | 12/1969 | Stevens . | |
| 3,618,613 | 11/1971 | Schulte | 604/282 |
| 3,924,632 | 12/1975 | Cook . | |
| 4,044,765 | 8/1977 | Kline . | |
| 4,052,989 | 10/1977 | Kline . | |
| 4,106,506 | 8/1978 | Koehn et al. . | |
| 4,184,497 | 1/1980 | Kolff et al. . | |
| 4,351,341 | 9/1982 | Goldberg et al. | 604/96 |
| 4,447,239 | 5/1984 | Krutten . | |
| 4,498,473 | 2/1985 | Gereg | 604/96 |
| 4,508,535 | 4/1985 | Joh et al. . | |
| 4,634,432 | 1/1987 | Kocak | 604/282 |
| 4,639,252 | 1/1987 | Kelly et al. . | |
| 4,676,229 | 6/1987 | Krasnicki et al. . | |
| 4,705,511 | 11/1987 | Kocak . | |
| 4,737,153 | 4/1988 | Shimamura et al. . | |
| 4,795,458 | 1/1989 | Regan | 606/191 |
| 4,848,344 | 7/1989 | Sos et al. . | |
| 4,946,466 | 8/1990 | Pinchuk et al. . | |
| 5,069,674 | 12/1991 | Fearnot et al. | 604/282 |
| 5,107,852 | 4/1992 | Davidson et al. | 604/282 |
| 5,190,520 | 3/1993 | Fenton, Jr. et al. | 604/282 |

Primary Examiner—John D. Yasko
Assistant Examiner—Perry E. Van Over
Attorney, Agent, or Firm—Lockwood, Alex, Fitzgibbon & Cummings

[57] ABSTRACT

A catheter and its method of use provide flexibility attributes while exhibiting torsional rigidity properties which are advantageous for transluminal treatments and analyses. The catheter includes a shaft component having a generally helically wound coil with a skin or webbing supported by the coil. The skin or webbing generally follows movement of the coil, including movement of adjacent coil windings toward and, in some instances, away from each other. The skin or webbing contributes negligibly to the resistance of the catheter to axially directed compressive forces, especially during implantation or insertion, and the catheter exhibits exceptional kink resistance through very tortuous vessels of the body.

24 Claims, 1 Drawing Sheet

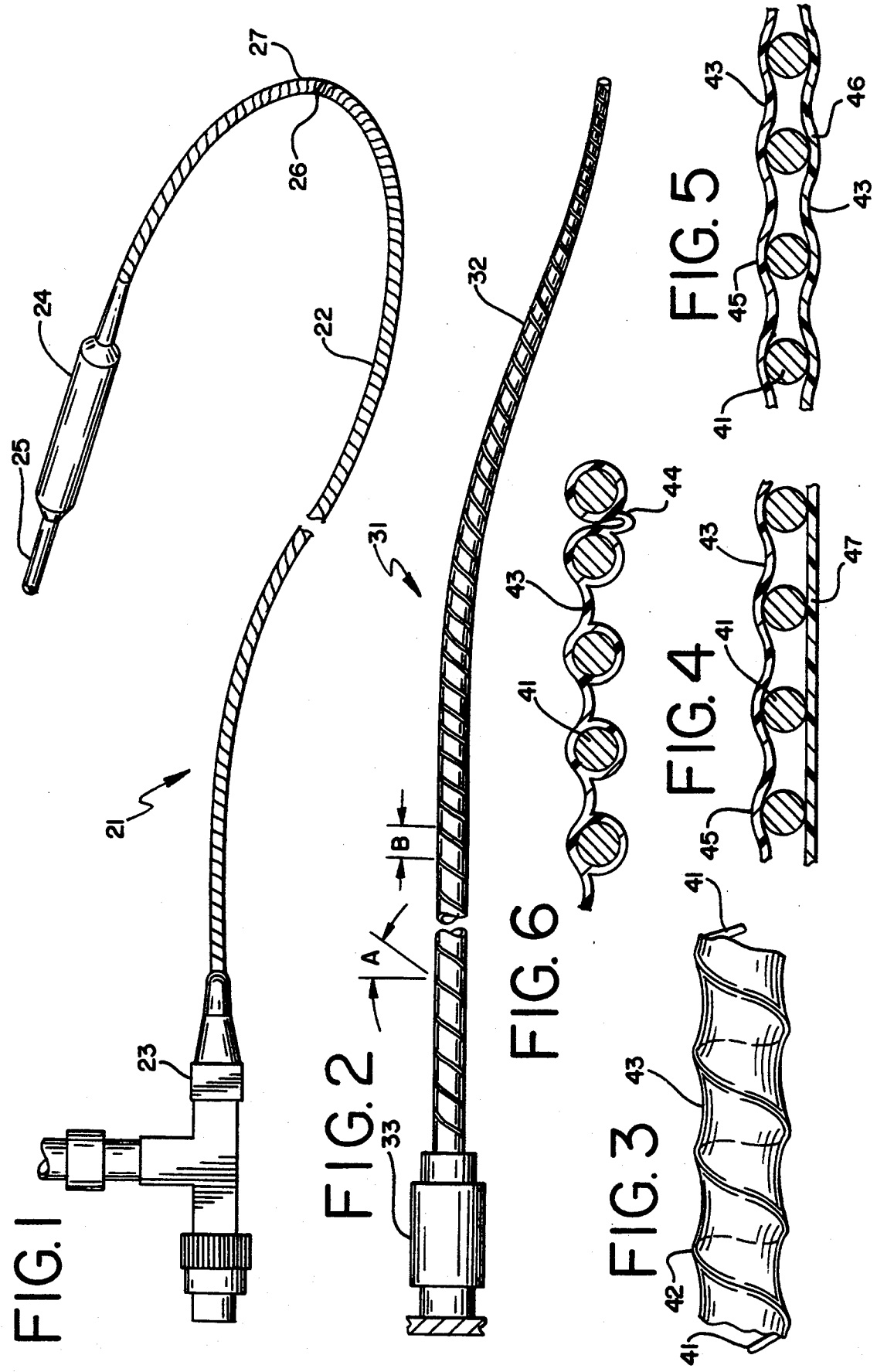

HELICALLY WOUND CATHETERS

BACKGROUND AND DESCRIPTION OF THE INVENTION

The present invention generally relates to medical catheters, more particularly to medical catheters wherein the elongated shaft of the catheter includes a helically wound coil component which provides the principal structural integrity of the catheter shaft at that location which enables it to perform as a catheter, including needed torsional rigidity and kink resistance. At the same time, the helically wound coil provides a structure which is extremely flexible in order to facilitate maneuvering during use, even through highly tortuous vessels of the body. A thin polymeric skin generally extends along the helically wound coil without substantially affecting the strength or maneuverability characteristics of the helically wound coil itself, such as its resistance to axially directed forces.

Numerous catheter types and styles are known and-/or used for any number of various medical procedures. Included are catheters for angioplasty procedures, including catheters incorporating so-called balloon components, other catheters for delivering medication or treatment or means for observation, analysis, detection and the like, as well as other catheter structures such as catheter sheath introducers. Often these catheter devices have a substantially small outer diameter. Typically, catheters for percutaneous transluminal coronary angioplasty procedures are of this small diameter variety. It is often necessary that catheters wind their way through various passageways within the human body, such as coronary passageways and branched veins. When balloon catheters are involved, it is at times necessary to have the balloon catheter exhibit a combination of torsional control and flexibility which permits and facilitates placement of the balloon at the precisely needed location in a very efficient and accurate manner. Because of the extremely small locations into which devices of this type are passed, it is often a primary objective to have the catheters exhibit extremely thin wall characteristics.

Heretofore, various catheter devices have been provided which exhibit particularly advantageous torsional rigidity and axial strength properties. Often these catheters achieve an especially thin-walled structure by being made of polymers having excellent torsional rigidity properties which are imparted to the catheter even when the polymeric catheter wall is especially thin. At times, catheters incorporate braiding to enhance the torsional control properties of the catheter. Generally helically shaped coils have also been used in an effort to attain these ends and objectives. When such braids or coils are used, they will usually serve to assist the structural properties of the cylindrical catheter shaft, often being embedded within the polymeric catheter shaft.

Typically, catheter shafts or devices which incorporate braids or helical coils achieve enhanced torsional control at the expense of flexibility of the type that enhances the maneuverability of the catheter. Wall thinness usually is also sacrificed. In some instances, these drawbacks are perfectly acceptable. However, in other circumstances, flexibility is the principal objective of the catheter or catheter component. There is a need for a catheter construction which can be tailored to meet especially stringent flexibility criteria and move through highly tortuous paths within the body while still providing torsional rigidity that is adequate for catheter use and also superior kink resistance, all without requiring an undesirable wall thickness.

In summary, the present invention provides catheter construction characteristics which exhibit exceptional flexibility and kink resistance while retaining adequate torsional control in order to provide a catheter shaft or body component that imparts maneuverability characteristics which are particularly advantageous for certain specific needs such as movement through tortuous body paths. Included is a shaft length constructed of a helically wound coil having a plurality of windings that are spaced apart from each other as wound. A polymer skin spans the windings and its function is primarily for the purpose of providing a barrier to fluids or liquids which is generally co-extensive with the cylinder defined by the helically wound coil. The skin is substantially thinner and less rigid than the helically wound coil and contributes negligibly to resistance of the catheter to axially directed forces.

It is a general object of the present invention to provide an improved catheter exhibiting exceptional flexibility while retaining adequate torsional control.

Another object of the present invention is to provide an improved angioscopic balloon catheter having an elongated shaft component made of a helically wound coil with a skin spanning adjacent windings without detrimentally affecting the mechanical properties of the coil.

Another object of this invention is to provide an improved catheter construction having a catheter shaft with helically coiled windings that are spaced from each other as wound and that vary such spacing when used.

Another object of the present invention is to provide a helically wound catheter made of a coil having a thin skin spanning coil windings but neither contributing substantially to catheter wall thickness nor contributing any significant resistance to compressive axial movement of the catheter shaft.

These and other objects, features and advantages of this invention will be clearly understood through a consideration of the following detailed description.

BRIEF DESCRIPTION OF THE DRAWINGS

The invention will be further elucidated in the following description with reference to the annexed drawings briefly described as follows.

FIG. 1 is a partial elevational and partial perspective view of a catheter having a helically wound shaft.

FIG. 2 is an elevational view of a different style of catheter incorporating a helically wound shaft.

FIG. 3 is an enlarged perspective view showing details of the helically wound construction of the present invention.

FIG. 4 is a cross-sectional view through an embodiment having two polymeric skin cylinders spanning adjacent helical windings of the coil.

FIG. 5 is a cross-sectional view of an embodiment similar to that illustrated in FIG. 4.

FIG. 6 is a cross-sectional view through another embodiment wherein the polymeric skin closely surrounds the coil windings as well as provides a thin web joining the windings.

DESCRIPTION OF THE PARTICULAR EMBODIMENTS

A catheter having a helically wound shaft is generally illustrated in FIG. 1 by reference numeral 21. This illustrated catheter generally includes a shaft 22 and a hub portion 23 of generally known construction. The particular catheter which is illustrated in FIG. 1 is suitable for balloon angioplasty procedures and includes a balloon assembly 24 and a tip portion 25. In this type of catheter, as is well known, the distal end portion of the catheter is maneuvered to the location of a lesion, after which the balloon is inflated (as shown in FIG. 1) to treat the lesion, inflation being carried out by the passage of suitable fluid into one of the ports illustrated in the hub portion 23 and through the catheter to the balloon assembly 24.

FIG. 2 illustrates another type of catheter, generally designated 31, which does not include a balloon assembly. It likewise includes an elongated shaft 32 and a hub portion 33 for attachment to suitable known devices. Catheters of this type can be made of the helically wound construction in accordance with the present invention particularly where exceptional flexibility is a prime consideration. Also, while it will be appreciated that FIG. 1 and FIG. 2 show catheters that have the helically wound construction substantially throughout the length of their respective shafts, portions of the shaft could exhibit a more conventional construction whereby the helically wound construction is provided along only a portion of the catheter shaft. In addition, tip portion 25 can include the helically wound construction.

Further details of the helically wound construction according the present invention are illustrated in FIG. 3. A helically wound coil 41 provides the structure and substantially all of the strength which is exhibited by the catheter shaft portion shown in FIG. 3. In an important aspect of this invention, the helically wound coil 41 is designed to provide virtually all of the strength and maneuverability properties required of the elongated catheter shaft or shaft component. These attributes are tailored according to the specific properties to be provided by the catheter. A polymeric skin 42 spans the distance between adjacent turns or windings of the helically wound coil 41. The skin 42 is substantially passive from a structural viewpoint. It is provided as a barrier for fluids, liquids and the like to substantially prevent unintentional passage of such substances either into or out of the lumen of the catheter. The skin 42, which preferably is very thin, is intended to prevent unintentional entry of body fluids into the lumen of the catheter while also providing a barrier to unintentional flow of fluids, such as those used to inflate an angiographic balloon assembly 24, out of the catheter and into the body of the patient. Skin 42 may also, in certain instances, provide lubricity properties to assist in passage, especially sliding movement, of catheter components with respect to each other.

It is intended that the skin 42 will not significantly interfere with the strength and flexibility of the helically wound coil 41. For example, as generally illustrated in FIG. 1, when the shaft 22 undergoes substantial bending, the spacing between adjacent turns or windings of the coil reduces on what might be termed the concave side of the curve, generally illustrated at 26, while the spacing between adjacent windings or turns on the convex side of the curve, illustrated at 27, remains the same or could even be increased somewhat. Such increase could be due either to stretching of the thin skin material itself or straightening of undulations, such as at 43, formed where the skin 42 spans the spacing between adjacent windings or turnings of the helical coil 41.

In addition, under some circumstances, and depending upon the axial resistance of the helically wound coil, the helically wound catheter shaft or portion will, from time to time, decrease in axial length during implantation and maneuvering within and through the body. In those instances when the catheter encounters resistance which is greater than the axial force imparted by the catheter and particularly by the helically wound coil 41, the coil will compress generally axially. Once the resistance is removed or overcome, the elastic memory of the helically wound coil will tend to return the catheter to its axial length and shape as wound. This can provide the benefit of having the helically wound coil impart a gentle springing action which, when coupled with its flexibility, enhance and facilitate movement around and beyond obstructions that can be encountered during catheterization procedures. This is generally a forwardly or distally directed springing action which is not so excessive or aggressive as to induce trauma substantially greater than that associated with previous catheterization and/or angioplasty procedures.

A primary component in achieving this objective is the provision of adequate spacing between adjacent turns or windings of the helically wound coil 41. Adequate spacing distance will be predetermined according to the desired properties of the catheter, particularly with respect to its desired resistance to axial compression and desired aggressiveness during implantation or insertion. Also relevant is the pitch angle of the helically wound coil 41 and the spring strength or elasticity of the coil material.

With reference to the pitch angle characteristic of the helically wound coil 41, reference is made to FIG. 2. Pitch angle A describes the angle by which each individual turn deviates from a plane transverse to the catheter shaft. When all other parameters are equal, such as coil diameter, shape, material and spring memory, a shallower or small pitch angle A will result in a lower resistance to coil collapse or compression when compared with a larger or more aggressive pitch angle A. Generally speaking, a larger pitch angle means that a larger portion of the springing forces of the coil are axially directed. Likewise, the larger the axially directed force, the greater resistance of the coil and thus of the catheter shaft component to axial compression. The resistance of the coil to axial compression of course largely determines the force needed to reduce the distance between adjacent windings and the force imparted by the coil to return to its as-coiled orientation after any degree of spring collapse has occurred. Accordingly, the pitch angle is a parameter of the structure of the present invention which can be varied in order to tailor a particular catheter shaft component by modifying its flexibility, bendability and aggressiveness.

Another parameter providing tailorability properties to the catheters is the modulus of elasticity of the material out of which the coil is made, as well as cross-sectional sizing and shaping of the coil. Materials exhibiting a stiff or relatively high modulus of elasticity will exhibit a greater resistance to bending and thus a decrease in flexibility for a given pitch angle and coil filament cross-sectional shape and size. Conversely, a coil material exhibiting a soft or relatively low modulus of elasticity will be more flexible, all other parameters being equal.

Another coil parameter that is available for tailorability purposes is the spacing between adjacent turns or windings, with a turn or winding being defined as any full 360° section of a coil. This spacing distance is illustrated by distance B in FIG. 2. Spacing distance B tends to be more significant to tailorability when the pitch angle and spring characteristics of the coil provide a relatively low level of resistance to axial compression of the coil, particularly when that resistance is so low as to allow for contact between adjacent windings, either for their full circumferential extent or for a section thereof, such as would be experienced during significant bending of the catheter, such as illustrated at 26 and 27 in FIG. 1. It will be appreciated that, the greater the spacing distance B, the greater will be the flexibility of the catheter or catheter component, all of the parameters and conditions being equal. Generally speaking, the spacing distance B between windings will be at least as great as the thickness of the filament material out of which the coil is constructed. Depending upon the flexibility desired and the other parameters as generally discussed herein, the spacing distance B could be up to about 20 times or greater of this filament cross-sectional size.

It will be appreciated that these various tailorability attributes of the catheter shaft construction in accordance with this invention are primarily dependent upon the particular parameters, properties and characteristics of the helically wound coil 41. In this regard, it is an important aspect of the invention that the skin component or components do not substantially modify these various parameters of the helically wound coil 41. In a very general sense, the skin material is a primarily passive component whose configuration and strength properties are virtually totally dependent upon the helically wound coil 41. For example, in those instances where adjacent coil windings generally engage one another, the skin collapses on itself, typically in a generally accordion-like manner such as illustrated at 44 in FIG. 6. It will be appreciated that the skin provides little resistance to the development of configurations such as that of the accordion bend 44. This passive or low strength characteristic of the skin is due to the properties and thickness of the material or materials out of which the skin is constructed.

The skin should be extremely flexible and could even be somewhat elastic. Its primary shape characteristic is that it will follow the shape and changing configuration of the helically wound coil 41. However, unless the skin is especially elastic, it will perform a structural function of limiting increase of spacing between adjacent windings, which can be of importance when explanting or removing the catheter. In any event, the skin typically has a thickness which is less than the cross-sectional thickness of the coil filament. At the same time, the skin component must be biocompatible and must have strength characteristics that will prevent pin-holing, cracking, tearing or the like throughout the useful life of the catheter. Also, when it is intended that pressurized fluids pass through the catheter shaft or shaft component in accordance with the invention, the skin material must be adequate to withstand anticipated fluid pressures, even under stress conditions which can be generated when the skin is forced to follow expansion and contraction of the helically wound coil.

The completed catheter has the important advantage of being kink resistant even when deployed through very tortuous vessels. This advantage is achieved by the important combination of the coil and skin as discussed herein.

With more specific reference to the particular embodiments illustrated in FIGS. 4, 5 and 6, variations on the skin component are illustrated thereby. Attachment can be by means of heat shrinking, adhesives, contact welding, dipping and the like. FIGS. 4 and 5 illustrate dual component thin skins having one component 45, typically the outermost component, which generally follows the rough contour of the helically wound coil 41 and includes undulations 43. The other skin 46 of the FIG. 5 embodiment also includes undulations 43 whereby both the inner and outer skin components generally follow the configuration of the helically wound coil. In FIG. 4, the other skin component 47 is taut and thus substantially right-cylindrical without undulations when the helically wound coil 41 is in its as-wound or initial configuration.

In the FIG. 6 embodiment, a single component of the skin joins adjacent coil windings. If desired, the skin can also encase the helically wound coil as generally shown in FIG. 6. This latter feature can enhance the mechanical attachment of the skin component to the helically wound coil. While in this embodiment, the skin can be of a substantially one-piece construction, it is also possible to have same be composed of a plurality of sheet components bonded together to form a skin which functions substantially as a one-piece component.

It will be understood that the embodiments of the present invention which have been described are illustrative of some of the applications of the principles of the present invention. Numerous modifications may be made by those skilled in the art without departing from the true spirit and scope of the invention.

I claim:
1. A medical device catheter, comprising:
   an elongated catheter shaft having an elongated shaft component;
   a hub component at a proximal location with respect to the elongated catheter shaft;
   said elongated shaft component including at least one section composed of an assembly of an elongated generally helically wound coil and a skin component supported thereby;
   said helically wound coil having a plurality of windings which traverse 360° of the coil from beginning to end of each said winding, each said winding being separated from an adjacent said winding by a predetermined spacing distance as wound throughout said shaft component one section to form spaces between adjacent windings, said generally helically wound coil being constructed of a filament having a selected thickness, said predetermined spacing distance as wound being at least about equal to said filament selected thickness such that adjacent windings of said coil are separated from each other throughout said shaft component one section by said spaces; and
   said skin component extending over said windings throughout said shaft component one section and flexibly spanning said spaces of said predetermined spacing distance as wound, said skin component having a negligible contribution to the resistance of the elongated shaft component to generally axially directed forces tending to compress the elongated shaft component and collapsing and entering into said spaces between said adjacent windings when such axially directed compression forces are applied to said one section;

whereby said assembly of coil and skin component is very kink resistant and facilitates movement through a highly tortuous path within a body.

2. The catheter in accordance with claim 1, wherein said skin component has a thickness less than said selected thickness of the coil filament.

3. The catheter in accordance with claim 1, wherein said skin component is a thin polymeric overskin which is suspended across the predetermined spacing distance as wound and between the adjacent windings of the generally helically wound coil.

4. The catheter in accordance with claim 1, wherein the skin component has undulations which generally follow the generally helically wound coil configuration as wound and when said predetermined spacing distance is reduced.

5. The catheter in accordance with claim 1, wherein said skin component is a thin webbing joining adjacent windings of said generally helically wound coil, whereby the configuration of the generally helically wound coil is easily discernable by external observation.

6. The catheter in accordance with claim 1, wherein said generally helically wound coil provides substantially all of the torsional rigidity and structural integrity of the shaft component.

7. The catheter in accordance with claim 1, wherein the skin component generally collapses on itself at locations between adjacent windings of the generally helically wound coil when said adjacent windings move generally toward one another.

8. The catheter in accordance with claim 1, wherein the skin component between adjacent windings of the generally helically wound coil stretches when the adjacent windings move away from each other to a distance greater than that of said predetermined spacing distance.

9. The catheter in accordance with claim 1, wherein a single web of skin component joins adjacent windings of the generally helically wound coil.

10. The catheter in accordance with claim 1, wherein a plurality of skin component webs join adjacent windings of the generally helically wound coil.

11. The catheter in accordance with claim 1, further including a balloon assembly along said elongated catheter shaft.

12. The catheter in accordance with claim 11, wherein said catheter is an angioscopic balloon catheter.

13. The catheter in accordance with claim 1, wherein said elongated shaft component extends substantially the full length of the elongated catheter shaft.

14. The catheter in accordance with claim 1, wherein said predetermined spacing distance as wound is tailored to vary between about one and about twenty times said filament selected thickness.

15. The catheter in accordance with claim 1, wherein said skin component is fixed to said coil.

16. A transluminal method for in vivo catheter treatment, comprising the steps of:

providing a catheter device having an elongated shaft component including at least one section having an elongated generally helically wound coil and a skin component supported on an outer surface of said coil, said coil providing the entire support for said skin component, the helically wound coil having a plurality of windings, adjacent ones of which are spaced from each other by a predetermined spacing distance as wound along the length of said shaft component one section to define spaces between adjacent windings;

transluminally inserting the catheter device within a body vessel and to a distal location within the body vessel at which a medical procedure is to be carried out;

said transluminally inserting step including advancing the catheter device in a generally distally oriented direction, said advancing step causing reduction in the predetermined spacing distance as wound between at least two adjacent windings of the catheter device along at least a section of the adjacent windings in response to interaction between the catheter device and the body vessel;

said advancing step including generally collapsing the skin component so that it enters into said spaces between said adjacent windings in response to said reduction of the predetermined spacing distance as wound between adjacent windings; and performing a medical procedure with respect to the body vessel at a location along the catheter device after having carried out said advancing step.

17. The transluminal method in accordance with claim 16, wherein said advancing step periodically causes said reduction in the predetermined spacing distance whereby a gentle springing action is provided by the catheter device during said advancing step.

18. The transluminal method in accordance with claim 16, wherein said advancing step at times causes an increase in the predetermined spacing distance as wound.

19. The transluminal method in accordance with claim 18, wherein the increase in predetermined spacing distance includes elongating a portion of the skin component.

20. The transluminal method in accordance with claim 16, wherein said in vivo treatment is a treatment of a lesion within the body vessel, the transluminally inserting step positions a balloon component along the elongated shaft component of the catheter device at the lesion location, and the performing step performs a treatment procedure on the lesion by operation of the catheter device which radially expands the balloon component of the catheter device.

21. The transluminal method in accordance with claim 16, wherein said skin component is fixed to said coil.

22. A medical device catheter, comprising:

an elongated shaft component and a hub component at a proximal location with respect to the shaft component;

said shaft component being composed of an assembly of an elongated generally helical coil and a skin component supported thereby extending from said hub component to a distal end of said shaft component, the coil comprising a plurality of windings which traverse 360° of rotation around said coil from beginning to end of each said winding, each of said windings being spaced apart from an adjacent winding by an intervening spacing of a predetermined distance throughout the length of said shaft component, said coil being formed from a continuous filament having a preselected thickness, said coil predetermined spacing distance being at least about as great as said filament thickness, whereby adjacent coil windings are separated from each other throughout said shaft component length by said intervening spacing, said coil providing a supporting skeleton for the skin component, said skin component extending along said shaft component and flexibly spanning said intervening spacing distance between said adjacent windings, said skin component having a thickness less than said coil filament preselected thickness, said skin component further having a negligible contribution to the resistance of the elongated shaft component to generally axially directed forces tending to compress the elongated shaft component and collapsing and entering into said intervening spacing when such axially directed forces arise during insertion of said catheter, whereby said assembly of coil and skin component is kink-resistant and facilitates movement through a highly tortuous path within a body.

23. A medical catheter of composite construction, comprising: a hub member; an elongated shaft member of predetermined extent extending away from the hub member and terminating in a distal end, the shaft member being defined by a continuous flexible coil formed from a wire stock of substantially constant thickness, the coil including a plurality of windings, each winding extending through 360° of rotation around said coil, said windings being disposed along the entire extent of said shaft member in a spaced-apart relationship whereby each said winding is separated from an adjacent winding by an intervening spacing to define a predetermined gap between each of said windings, the gap having a minimum distance between said adjacent windings which varies between a minimum of one coil winding wire stock thickness and a maximum of twenty coil winding wire stock thicknesses; and, at least one elongated, flexible skin covering all of an outer surface of said entire extent of said shaft member, the skin covering being supported on said shaft member by said coil windings and spanning each of said gaps between adjacent windings, said skin covering offering substantially no resistance to axial compressive forces exerted upon said shaft member, and collapsing and entering into said gaps during insertion of said catheter into a body vessel.

24. The catheter of claim 23, wherein a portion of said one skin covering envelops each of said coil windings.

* * * * *